US00PP09878P

United States Patent [19]

Jacobsen

[11] Patent Number: Plant 9,878

[45] Date of Patent: Apr. 29, 1997

[54] POINSETTIA PLANT PETERSTAR WHITE

[75] Inventor: Peter Jacobsen, deceased, late of Skibby, Denmark, by Aase Jacobsen, executrix

[73] Assignee: Paul Ecke Ranch, Inc., Encinitas, Calif.

[21] Appl. No.: 500,767

[22] Filed: Jul. 10, 1995

[51] Int. Cl.[6] ..... A01H 5/00

[52] U.S. Cl. ..... Plt./86.2

[58] Field of Search ..... Plt./86.2

[56] References Cited

U.S. PATENT DOCUMENTS

P.P. 7,250 6/1990 Gutbien ..... Plt./86.2

*Primary Examiner*—James R. Feyrer

*Attorney, Agent, or Firm*—Arnold, White & Durkee

[57] ABSTRACT

Poinsettia 'Peterstar White' is a new cultivar, distinguished by white bracts, large flowers, strong stems and self-branching characteristics. 'Peterstar White' is a sport of the red bracted 'Peterstar' (U.S. Plant Pat. No. 8,259) with the same flowering response and cultural requirements. The new plant produces a very desirable branched flowering pot plant. The new plant is resistant to epinasty after being confined to shipping containers. The post-production foliage and bract retention is good.

1 Drawing Sheet

BACKGROUND OF THE NEW PLANT

This new poinsettia cultivar originated as a white bracted sport of 'Peterstar' (U.S. Plant Pat. No. 8,259) in my greenhouse in Skibby, Denmark in 1991. It was induced through irradiation of vegetative plants with 2500 rads of gamma radiation, and was selected from about 200 mutants so produced, because of its white bracts, large flowers, strong stems, self-branching, and dark green leaves, traits which help distinguish it from other poinsettia cultivars, and seemed to make it a desirable plant for commercial greenhouse production. 'Peterstar White' differed from its parent 'Peterstar' in having creamy white bracts as compared to the bright red bracts of 'Peterstar'. 'Peterstar White' resembles poinsettia '21–85' (U.S. Plant Pat. No. 7,250) but distinctly differs in color, growth habit and flowering response.

Phenotypically, 'Peterstar White' resembles its parent 'Peterstar' (U.S. Plant Pat. No. 8,259) except for those traits associated with color mutations. The morphology, plant vigor and flowering response times are similar in 'Peterstar White' and 'Peterstar'. The flower bract color of 'Peterstar White' is creamy white near R.H.S. 8D. In contrast, the red bract color of 'Peterstar' is near R.H.S. 46B. The leaf petiole color of 'Peterstar White' is light green while that of 'Peterstar White' is red.

After selection, 'Peterstar White' was vegetatively reproduced from stem cuttings for test purposes in Encinitas, Calif. By subjecting clones of this plant to successive generations of vegetation propagation, it was demonstrated that the distinctive characteristics of 'Peterstar White' held true from generation to generation. Grown under the same greenhouse environment, 'Peterstar White' has the same growth habit and flowering response time as the parent plant 'Peterstar'.

DESCRIPTION OF THE PHOTOGRAPHS

Poinsettia 'Peterstar White' is illustrated in the accompanying color photographs.

The upper photo is a side view of 3 single stem plants per pot in full flower.

The lower photo is a top view of the same plants showing flower and bract formation.

DESCRIPTION OF THE PLANT

The following is a detailed description of this new poinsettia as observed in Encinitas, Calif., U.S.A. during December 1994. Observations were recorded from flowering plants, grown as 3 single stem plants per pot. The pot was 14 cm in diameter and 11 cm in height. Color designations are compared to the 1986 edition of R.H.S. Colour Chart, first published in 1966 by The Royal Horticultural Society, London, England.

THE PLANT

The following chart summarizes some of the differences between 'Peterstar White' and poinsettia '21–85'.

| Plant | 'Peterstar white' | '21–85' |
|---|---|---|
| Height | 35 cm | 40 cm |
| Flower Response | 8.5 weeks | 9 weeks |
| Blooming date (Southern California) | November 25 | November 30 |
| Flowers | Sterile | Fertile |
| Bract Color | RHS 8D | RHS1D-155A |
| Internode length | 16–17 mm | 20 mm |

Origin: Sport of 'Peterstar' (U.S. Plant Pat. No. 8,259), induced through irradiation of vegetative plants with 2500 rads of gamma radiation.

Classification:

*Botanic.*—*Euphorbia pulcherrima* Willd.

*Common name.*—Poinsettia.

*Cultivar name.*—'Peterstar White'.

Form: Shrub.

Height: Medium.

Growth habit: As a single stemmed plant, upright and vigorous with self-branching side shoots. The application of a chemical growth retardant may not be needed to restrict height for commercial pot plant production. I observed 3 unpinched plants in a pot with an overall height of 35 cm and an overall width of 45 cm. The bract diameter of individual flowers was 30 cm. The compactness of 'Peterstar White' is demonstrated by the internode length. Internode lengths of flowering plants of 'Peterstar White' are 16–17 mm.

Branching: Axillary branches will develop and terminate in a flower without pinching. However, it is usually desirable to pinch 'Peterstar White' before flower induction and remove all terminal dominance. Then, all axillary branches will develop uniformly and at a faster rate.

Growth rate: Rooting of stem cutting occurs in 12–18 days under intermittent mist.

Flowering: The plant will flower in eight to nine weeks under continuous long night conditions and night temperatures of about 16–18° C. Like its parent, ('Peterstar'), 'Peterstar White' will be in full bloom in late November in Southern California under natural daylength conditions.

Foliage: The foliage was clean and uniformly dark green from bottom to top of the plant. The leaves were of medium size, leaf blades typically being 13–14 cm long and 8–9 cm wide with leaf petioles 4–6 cm long.

*Leaf shape.*—Typical leaves are ovate with obtuse bases and acuminate tips. Leaf margins are mostly entire. An occasional lower leaf is modestly lobed on either side of the leaf blade.

*Leaf surface.*—The upper surface is glabrous and the under surface is slight pubescent.

*Color.*—Upper side — Green, slightly darker than R.H.S 147A. Under side — Green, near R.H.S 147B.

*Retention.*—The foliage retention is good even under low light intensities in the consumer's home.

Bracts: Generally there were 17–21 white bracts of various sizes subtending the cyathia. The primary bracts had blades typically 14–16 cm long and 10–11 cm wide with petioles 2–3 cm long.

*Shape.*—Primary bracts are ovate with acute bases and acuminate tips. Leaf margins are entire or weakly lobed with 1 small indention on either side of the bract. Secondary bracts are ovate to elliptic and have entire margins.

*Surface.*—The bract surface is slightly rugose.

*Color.*—Upper side — Creamy white, near R.H.S 8D. Under side — Creamy white, near R.H.S. 8D.

Flowers: Generally, 18–22 cyathia (flowers) are present when the plant is in full bloom. Each cyathium is about 6–7 mm long and 5–6 mm wide, green in color, and fringed yellow at the distal end. Usually one, but occasionally two, yellow nectar cups protrude from the side of each cyathium. The flower pedicel is also green and about 5 mm in length. The stamens protruding from the cyathia are white and trifurcate. 'Peterstar White' has abortive anthers, is male sterile and possible female sterile, as seed set has not been seen on this cultivar. Cyathia retention is about three weeks beyond the time the flower is fully mature.

*Nectar exudate.*—Present, abundant.

*Seed formation.*—No seed set observed.

*Fertility.*—Flowers may be sterile.

Post production: 'Peterstar White' is resistant to epinasty after being confined to shipping containers. The foliage and bract retention is good.

What is claimed is:

1. A new and distinct poinsettia cultivar, substantially as herein shown and described, distinguished by its strong stems, white bracts, self-branching, large flowers and good leaf and bract retention in the consumer environment.

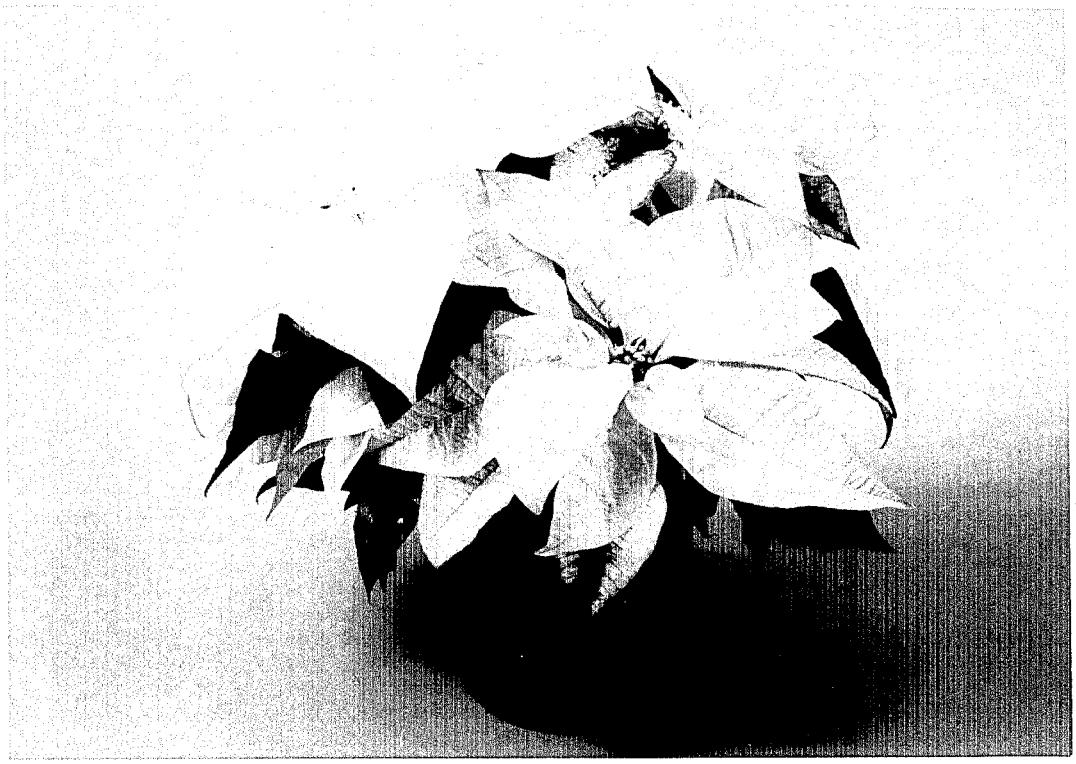
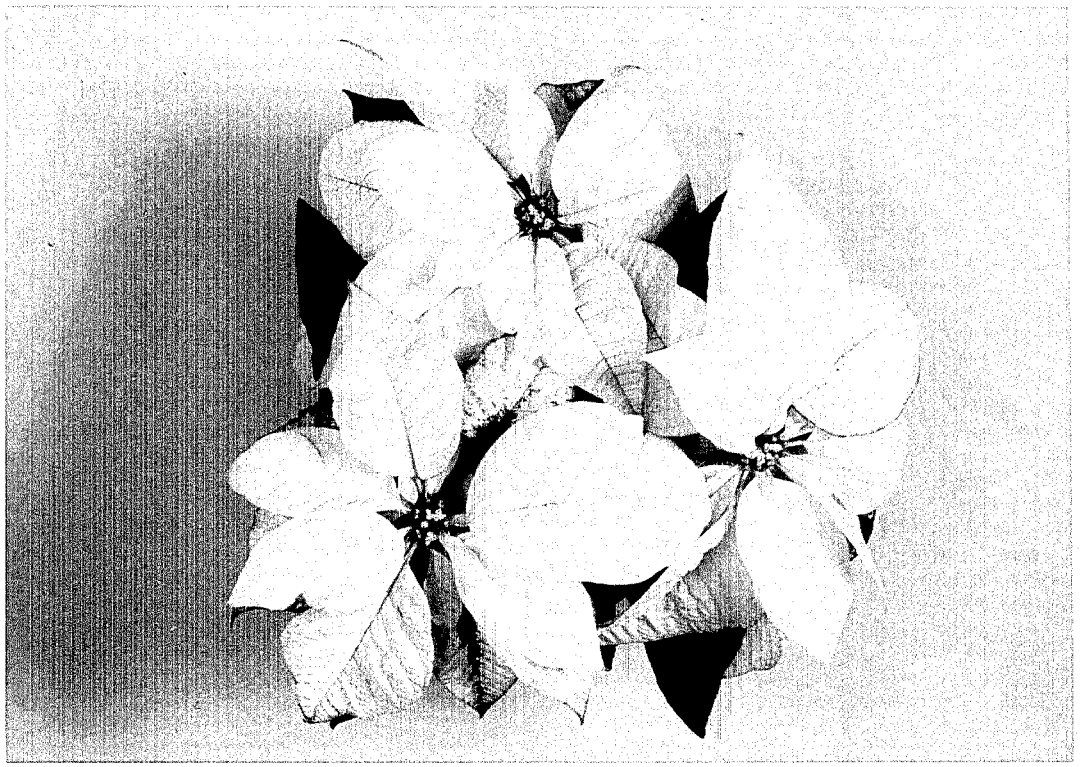

* * * * *